United States Patent
Wu et al.

(10) Patent No.: US 10,988,550 B2
(45) Date of Patent: Apr. 27, 2021

(54) METHOD FOR PREPARING RESISTANT DEXTRIN BY USING A STARCH BRANCHING ENZYME AND A CYCLODEXTRIN GLYCOSYLTRANSFERASE

(71) Applicants: Jing Wu, Wuxi (CN); Sheng Chen, Wuxi (CN); Jun Liu, Wuxi (CN)

(72) Inventors: Jing Wu, Wuxi (CN); Sheng Chen, Wuxi (CN); Jun Liu, Wuxi (CN)

(73) Assignee: Jiangnan University, Wuxi (CN)

( * ) Notice: Subject to any disclaimer, the term of this patent is extended or adjusted under 35 U.S.C. 154(b) by 0 days.

(21) Appl. No.: 16/196,768

(22) Filed: Nov. 20, 2018

(65) Prior Publication Data

US 2019/0248926 A1 Aug. 15, 2019

(30) Foreign Application Priority Data

Feb. 12, 2018 (CN) .......................... 201810145525.2

(51) Int. Cl.
| | |
|---|---|
| *C08B 30/18* | (2006.01) |
| *A23L 29/269* | (2016.01) |
| *C12P 19/04* | (2006.01) |
| *C08L 3/02* | (2006.01) |
| *C08B 31/00* | (2006.01) |

(52) U.S. Cl.
CPC ............ *C08B 30/18* (2013.01); *A23L 29/273* (2016.08); *C08B 31/00* (2013.01); *C08L 3/02* (2013.01); *C12P 19/04* (2013.01); *C12Y 204/01019* (2013.01)

(58) Field of Classification Search
None
See application file for complete search history.

(56) References Cited

FOREIGN PATENT DOCUMENTS

CN 103045701 * 4/2013

OTHER PUBLICATIONS

Chica et al. Curr Opin Biotechnol. Aug. 2005;16(4):378-84. (Year: 2005).*
Singh et al. Curr Protein Pept Sci. 2017, 18, 1-11 (Year: 2017).*
Aliasgharzadeh et al. Br J Nutr. Jan. 28, 2015;113(2):321-30 (Year: 2015).*
Accession Q475E7. Sep. 13, 2005 (Year: 2005).*
Suzuki et al. Biochim Biophys Acta. May 2015;1854(5):476-84. Epub Feb. 27, 2015 (Year: 2015).*
Li et al. Int J Biol Macromol. Feb. 2018;107(Pt B):1758-1764. Epub Oct. 10, 2017. (Year: 2017).*
Bai et al. Carbohydr Polym. Oct. 20, 2016;151:426-433. Epub May 20, 2016. (Year: 2016).*
Liu Jun et al. "Recombinant expression of Thermus thermophilus branching enzyme and its use in the preparation of resistant dextrins", Liu Jun et al., Food Industry Technology, vol. 38, No. 24, pp. 79-83, published Sep. 2, 2017 (Year: 2017).*
First Office Action by the State Intellectual Property Office of People's Republic of China dated Jan. 6, 2020 (Year: 2020).*
Haliping. "Food Additives", edited by Haliping, China Agricultural University Press, pp. 243-244, 3rd edition, Jun. 2016 (Year: 2016).*
Accession CP000088. Jan. 28, 2014 (Year: 2014).*

* cited by examiner

*Primary Examiner* — Christian L Fronda
(74) *Attorney, Agent, or Firm* — Lili Chen

(57) ABSTRACT

Disclosed is a method for preparing a resistant dextrin product by using compound enzyme treatment. Starch is first subjected to high-temperature acidolysis to obtain pyrodextrin which is used as the substrate for the enzyme treatment. A compound enzyme reaction system including a starch branching enzyme and a CGTase is used for preparing the resistant dextrin product. The starch branching enzyme and the CGTase are added simultaneously or sequentially to treat the pyrodextrin to further increase the content of the resistant component in the product. The content of the resistant component of the enzyme treated product reaches up to 65.3%, a 21.3% increase from that of the pyrodextrin before the enzyme treatment.

14 Claims, 10 Drawing Sheets

Specification includes a Sequence Listing.

SEQUENCE LISTING

```
<160> NUMBER OF SEQ ID NOS: 5

<210> SEQ ID NO 1
<211> LENGTH: 2250
<212> TYPE: DNA
<213> ORGANISM: artificial sequence
<220> FEATURE:
<223> OTHER INFORMATION: Synthetic Sequence

<400> SEQUENCE: 1
gtgaccgccc ggcctgcagt ccgccaaccc gctggcctgc cctgcccgca accctgcaac      60
cggtacggat atccgatgac caacgcactc ctcgctgaaa tcgacgccct ggtcgctggc     120
acccaccaca acccgcacgc cctgctcggc gcgcatcccg gcccggaagg ggtgtgggtg     180
cgtgccttgc gcccgctcgc ccgctccgtg cacgtgctcc tcgccaacgg cagccgggtc     240
gaacttcccc acctgcacaa aggcgtgttc gccggggtgg ttccgggtgc cgaagtcccc     300
gactaccggc tggtggtgcg ctacgacgac ggcaccgagc tcaccgtgga cgaccoctac     360 cggcacctgc ccactctcgg agagctcgac atccacctca tccaggaagg gcggcacgaa     420
gaactgtggc gcgtgctcgg cgcgcacacc aaacgcttcc cttctgtcct gggcgacacg     480
gaagggaccg cgttcaccgt gtgggcgccc aacgcccgcg gggtacgggt gattggggac     540
ttcaaccact gggacggcac tggccacccc atgcgttcgc tcggctcctg cggggtgtgg     600
gagctgttca tccccggggt cggcgacggt acccggtaca agtaccaggt gctcggcgcc     660
gacggagtgt ggcgggagaa agccgacccg gtggcgttcg ccacccaggc gccgccagag     720
accgcgtccg tggtgttcac ctcccgctac acctggcagg acgacgagtg gctgacgcag     780
cgcgccgccg ctgacctgca ccgcaagccg atgagcatct acgaggtgca cctcggttcg     840
tggcggcccg gcctgtccta ccgggagctt gccgaccagc tcgtggacta cgtccgcgag     900
ctggggttca cgcacgtgga attcctgccg gtcgcggagc acccgttcgg cggctcgtgg     960
ggctaccagg tcacctccta ttacgcgccc accgcccggt tcggctcccc cgacgacttc    1020
```

```
cggtacctgg tcgaccgcct ccaccaggcg gggatcgggg tgttcctgga ctgggtgccc    1080
gcgcacttcc cgaaagacga ctgggcgcta tcccgcttcg acggcaccgc cctgtacgag    1140
cacccggacc cgcgccgcgg catccacccc gactgggaca cgctgatctt caactacggc    1200
cgcaccgagg tccgcaactt tctggtcgcc aacgcactgt tctggctgga agagttccac    1260
atcgacgggc tgcgcgtgga cgcggtggct tccatgctct acctggacta ctcccgggag    1320
tccggccagt gggagcccaa cgcctacggc gggcgggaga acctggatgc catcgacttc    1380
ctgcgggagc tcaacgccac cgcctaccgc cgcaaccccg aatcgcgat gatcgccgag    1440 gaatccaccg cctggcccgg ggtgaccgcc agcaccgata cgggagggct cggcttcggg    1500
ttcaagtgga acatggggtg gatgcacgac accctgtcct acctgcagca cgaccccgtc    1560
caccggcagt accaccacaa cgaagtcacc ttctccatgg tgtacgccta cagcgagaac    1620
tatgtgctgc cgctctccca cgacgaagtc gtgcacggca gaggtcgct gctgtacaag    1680 atgccgggga acgagtggca gcgctgcgcg aacctgcggg cgctcctggc ctacatgtgg    1740
gcgcacccag gcaaacagct cctgttcatg ggcaacgaga tcgcccaagg cgacgagtgg    1800
tcgcacgacg ccggggtgca gtggtggctg ctgcgctacc ccaccatgc cgggatgcgc    1860 cggctcgtcg ccgacctcaa ccggctgtac cggaacacgc gggcgctgtg gagccaagac    1920
acggtcccgg aggggttcac ctggttggac ggcggtgacg cgagcggcaa cacgctgtcg    1980
tttctgcggt ggggagacga cgggtcggtc ctggcctgcc tcgtgaactt cagcggccgc    2040
ccgcacccgg agcgccgggt cggcctgccc tatgcgggcc ggtggcggga tcctcaac    2100 acggacgccg tgctttacgg cggcagcggc gtctcgcagc cggggatcat cgaggcctcc    2160
gaggagacgc cgtggcaggg ccagcccgct tccgctctgg tgacctaccc gccgctgggg    2220
gtgtcctggc tggtgttcga cgggacgtga                                    2250
```

<210> SEQ ID NO 2
<211> LENGTH: 749
<212> TYPE: PRT
<213> ORGANISM: Artificial Sequence
<220> FEATURE:
<223> OTHER INFORMATION: Synthethic Sequence

<400> SEQUENCE: 2

```
Met Thr Ala Arg Pro Ala Val Arg Gln Pro Ala Gly Leu Pro Cys Pro
1               5                   10                  15

Gln Pro Cys Asn Arg Tyr Gly Tyr Pro Met Thr Asn Ala Leu Leu Ala
            20                  25                  30

Glu Ile Asp Ala Leu Val Ala Gly Thr His His Asn Pro His Ala Leu
        35                  40                  45

Leu Gly Ala His Pro Gly Pro Glu Gly Val Trp Val Arg Ala Leu Arg
    50                  55                  60

Pro Leu Ala Arg Ser Val His Val Leu Leu Ala Asn Gly Ser Arg Val
65                  70                  75                  80

Glu Leu Pro His Leu His Lys Gly Val Phe Ala Gly Val Val Pro Gly
                85                  90                  95

Ala Glu Val Pro Asp Tyr Arg Leu Val Val Arg Tyr Asp Asp Gly Thr
            100                 105                 110

Glu Leu Thr Val Asp Asp Pro Tyr Arg His Leu Pro Thr Leu Gly Glu
        115                 120                 125

Leu Asp Ile His Leu Ile Gln Glu Gly Arg His Glu Glu Leu Trp Arg
    130                 135                 140
```

```
Val Leu Gly Ala His Thr Lys Arg Phe Pro Ser Val Leu Gly Asp Thr
145                 150                 155                 160

Glu Gly Thr Ala Phe Thr Val Trp Ala Pro Asn Ala Arg Gly Val Arg
                165                 170                 175

Val Ile Gly Asp Phe Asn His Trp Asp Gly Thr Gly His Pro Met Arg
            180                 185                 190

Ser Leu Gly Ser Cys Gly Val Trp Glu Leu Phe Ile Pro Gly Val Gly
        195                 200                 205

Asp Gly Thr Arg Tyr Lys Tyr Gln Val Leu Gly Ala Asp Gly Val Trp
    210                 215                 220

Arg Glu Lys Ala Asp Pro Val Ala Phe Ala Thr Gln Ala Pro Pro Glu
225                 230                 235                 240

Thr Ala Ser Val Val Phe Thr Ser Arg Tyr Thr Trp Gln Asp Asp Glu
                245                 250                 255

Trp Leu Thr Gln Arg Ala Ala Ala Asp Leu His Arg Lys Pro Met Ser
                260                 265                 270

Ile Tyr Glu Val His Leu Gly Ser Trp Arg Pro Gly Leu Ser Tyr Arg
            275                 280                 285

Glu Leu Ala Asp Gln Leu Val Asp Tyr Val Arg Glu Leu Gly Phe Thr
290                 295                 300

His Val Glu Phe Leu Pro Val Ala Glu His Pro Phe Gly Gly Ser Trp
305                 310                 315                 320

Gly Tyr Gln Val Thr Ser Tyr Tyr Ala Pro Thr Ala Arg Phe Gly Ser
                325                 330                 335

Pro Asp Asp Phe Arg Tyr Leu Val Asp Arg Leu His Gln Ala Gly Ile
                340                 345                 350

Gly Val Phe Leu Asp Trp Val Pro Ala His Phe Pro Lys Asp Asp Trp
            355                 360                 365

Ala Leu Ser Arg Phe Asp Gly Thr Ala Leu Tyr Glu His Pro Asp Pro
        370                 375                 380

Arg Arg Gly Ile His Pro Asp Trp Asp Thr Leu Ile Phe Asn Tyr Gly
385                 390                 395                 400

Arg Thr Glu Val Arg Asn Phe Leu Val Ala Asn Ala Leu Phe Trp Leu
                405                 410                 415

Glu Glu Phe His Ile Asp Gly Leu Arg Val Asp Ala Val Ala Ser Met
                420                 425                 430

Leu Tyr Leu Asp Tyr Ser Arg Glu Ser Gly Gln Trp Glu Pro Asn Ala
            435                 440                 445

Tyr Gly Gly Arg Glu Asn Leu Asp Ala Ile Asp Phe Leu Arg Glu Leu
450                 455                 460

Asn Ala Thr Ala Tyr Arg Arg Asn Pro Gly Ile Ala Met Ile Ala Glu
465                 470                 475                 480

Glu Ser Thr Ala Trp Pro Gly Val Thr Arg Ser Thr Asp Thr Gly Gly
                485                 490                 495

Leu Gly Phe Gly Phe Lys Trp Asn Met Gly Trp Met His Asp Thr Leu
            500                 505                 510

Ser Tyr Leu Gln His Asp Pro Val His Arg Gln Tyr His His Asn Glu
        515                 520                 525

Val Thr Phe Ser Met Val Tyr Ala Tyr Ser Glu Asn Tyr Val Leu Pro
    530                 535                 540

Leu Ser His Asp Glu Val Val His Gly Lys Arg Ser Leu Leu Tyr Lys
545                 550                 555                 560

Met Pro Gly Asn Glu Trp Gln Arg Cys Ala Asn Leu Arg Ala Leu Leu
```

```
                    565                 570                 575
Ala Tyr Met Trp Ala His Pro Gly Lys Gln Leu Leu Phe Met Gly Asn
            580                 585                 590

Glu Ile Ala Gln Gly Asp Glu Trp Ser His Asp Ala Gly Val Gln Trp
        595                 600                 605

Trp Leu Leu Arg Tyr Pro His His Ala Gly Met Arg Arg Leu Val Ala
        610                 615                 620

Asp Leu Asn Arg Leu Tyr Arg Asn Thr Arg Ala Leu Trp Ser Gln Asp
625                 630                 635                 640

Thr Val Pro Glu Gly Phe Thr Trp Leu Asp Gly Asp Ala Ser Gly
            645                 650                 655

Asn Thr Leu Ser Phe Leu Arg Trp Gly Asp Gly Ser Val Leu Ala
            660                 665                 670

Cys Leu Val Asn Phe Ser Gly Arg Pro His Pro Glu Arg Val Gly
            675                 680                 685

Leu Pro Tyr Ala Gly Arg Trp Arg Glu Ile Leu Asn Thr Asp Ala Val
            690                 695                 700

Leu Tyr Gly Gly Ser Gly Val Ser Gln Pro Gly Ile Ile Glu Ala Ser
705                 710                 715                 720

Glu Glu Thr Pro Trp Gln Gly Gln Pro Ala Ser Ala Leu Val Thr Tyr
                725                 730                 735

Pro Pro Leu Gly Val Ser Trp Leu Val Phe Asp Gly Thr
            740                 745

<210> SEQ ID NO 3
<211> LENGTH: 24
<212> TYPE: DNA
<213> ORGANISM: artificial sequence
<220> FEATURE:
<223> OTHER INFORMATION: synthetic sequence

<400> SEQUENCE: 3
ccatatgacc gcccggcctg cagt                                            24

<210> SEQ ID NO 4
<211> LENGTH: 29
<212> TYPE: DNA
<213> ORGANISM: artificial sequence
<220> FEATURE:
<223> OTHER INFORMATION: synthetic sequence

<400> SEQUENCE: 4
caagctttca cgtcccgtcg aacaccagc                                       29

<210> SEQ ID NO 5
<211> LENGTH: 680
<212> TYPE: PRT
<213> ORGANISM: Geobacillus stearothermophilus

<400> SEQUENCE: 5

Ala Gly Asn Leu Asn Lys Val Asn Phe Thr Ser Asp Val Val Tyr Gln
1               5                   10                  15

Ile Val Val Asp Arg Phe Val Asp Gly Asn Thr Ser Asn Asn Pro Ser
            20                  25                  30

Gly Ala Leu Phe Ser Ser Gly Cys Thr Asn Leu Arg Lys Tyr Cys Gly
        35                  40                  45

Gly Asp Trp Gln Gly Ile Ile Asn Lys Ile Asn Asp Gly Tyr Leu Thr
    50                  55                  60
```

-continued

Asp Met Gly Val Thr Ala Ile Trp Ile Ser Gln Pro Val Glu Asn Val
65              70                  75                  80

Phe Ser Val Met Asn Asp Ala Ser Gly Ser Ala Ser Tyr His Gly Tyr
            85                  90                  95

Trp Ala Arg Asp Phe Lys Lys Pro Asn Pro Phe Phe Gly Thr Leu Ser
            100                 105                 110

Asp Phe Gln Arg Leu Val Asp Ala Ala His Ala Lys Gly Ile Lys Val
            115                 120                 125

Ile Ile Asp Phe Ala Pro Asn His Thr Ser Pro Ala Ser Glu Thr Asn
        130                 135                 140

Pro Ser Tyr Met Glu Asn Gly Arg Leu Tyr Asp Asn Gly Thr Leu Leu
145                 150                 155                 160

Gly Gly Tyr Thr Asn Asp Ala Asn Met Tyr Phe His His Asn Gly Gly
                165                 170                 175

Thr Thr Phe Ser Ser Leu Glu Asp Gly Ile Tyr Arg Asn Leu Phe Asp
            180                 185                 190

Leu Ala Asp Leu Asn His Gln Asn Pro Val Ile Asp Arg Tyr Leu Lys
        195                 200                 205

Asp Ala Val Lys Met Trp Ile Asp Met Gly Ile Asp Gly Ile Arg Met
210                 215                 220

Asp Ala Val Lys His Met Pro Phe Gly Trp Gln Lys Ser Leu Met Asp
225                 230                 235                 240

Glu Ile Asp Asn Tyr Arg Pro Val Phe Thr Phe Gly Glu Trp Phe Leu
            245                 250                 255

Ser Glu Asn Glu Val Asp Ala Asn Asn His Tyr Phe Ala Asn Glu Ser
            260                 265                 270

Gly Met Ser Leu Leu Asp Phe Arg Phe Gly Gln Lys Leu Arg Gln Val
            275                 280                 285

Leu Arg Asn Asn Ser Asp Asn Trp Tyr Gly Phe Asn Gln Met Ile Gln
        290                 295                 300

Asp Thr Ala Ser Ala Tyr Asp Glu Val Leu Asp Gln Val Thr Phe Ile
305                 310                 315                 320

Asp Asn His Asp Met Asp Arg Phe Met Ile Asp Gly Gly Asp Pro Arg
            325                 330                 335

Lys Val Asp Met Ala Leu Ala Val Leu Leu Thr Ser Arg Gly Val Pro
            340                 345                 350

Asn Ile Tyr Tyr Gly Thr Glu Gln Tyr Met Thr Gly Asn Gly Asp Pro
        355                 360                 365

Asn Asn Arg Lys Met Met Ser Ser Phe Asn Lys Asn Thr Arg Ala Tyr
        370                 375                 380

Gln Val Ile Gln Lys Leu Ser Ser Leu Arg Arg Asn Asn Pro Ala Leu
385                 390                 395                 400

Ala Tyr Gly Asp Thr Glu Gln Arg Trp Ile Asn Gly Asp Val Tyr Val
            405                 410                 415

Tyr Glu Arg Gln Phe Gly Lys Asp Val Val Leu Val Ala Val Asn Arg
            420                 425                 430

Ser Ser Ser Ser Asn Tyr Ser Ile Thr Gly Leu Phe Thr Ala Leu Pro
        435                 440                 445

Ala Gly Thr Tyr Thr Asp Gln Leu Gly Gly Leu Leu Asp Gly Asn Thr
        450                 455                 460

Ile Gln Val Gly Ser Asn Gly Ser Val Asn Ala Phe Asp Leu Gly Pro
465                 470                 475                 480

Gly Glu Val Gly Val Trp Ala Tyr Ser Ala Thr Glu Ser Thr Pro Ile

-continued

```
                        485                     490                     495
Ile Gly His Val Gly Pro Met Met Gly Gln Val Gly His Gln Val Thr
            500                     505                     510

Ile Asp Gly Glu Gly Phe Gly Thr Asn Thr Gly Thr Val Lys Phe Gly
            515                     520                     525

Thr Thr Ala Ala Asn Val Val Ser Trp Ser Asn Asn Gln Ile Val Val
    530                     535                     540

Ala Val Pro Asn Val Ser Pro Gly Lys Tyr Asn Ile Thr Val Gln Ser
545                     550                     555                     560

Ser Ser Gly Gln Thr Ser Ala Ala Tyr Asp Asn Phe Glu Val Leu Thr
                565                     570                     575

Asn Asp Gln Val Ser Val Arg Phe Val Val Asn Asn Ala Thr Thr Asn
                580                     585                     590

Leu Gly Gln Asn Ile Tyr Ile Val Gly Asn Val Tyr Glu Leu Gly Asn
                595                     600                     605

Trp Asp Thr Ser Lys Ala Ile Gly Pro Met Phe Asn Gln Val Val Tyr
            610                     615                     620

Ser Tyr Pro Thr Trp Tyr Ile Asp Val Ser Val Pro Glu Gly Lys Thr
625                     630                     635                     640

Ile Glu Phe Lys Phe Ile Lys Lys Asp Ser Gln Gly Asn Val Thr Trp
                645                     650                     655

Glu Ser Gly Ser Asn His Val Tyr Thr Thr Pro Thr Asn Thr Thr Gly
                660                     665                     670

Lys Ile Ile Val Asp Trp Gln Asn
                675                     680
```

METHOD FOR PREPARING RESISTANT DEXTRIN BY USING A STARCH BRANCHING ENZYME AND A CYCLODEXTRIN GLYCOSYLTRANSFERASE

CROSS-REFERENCES AND RELATED APPLICATIONS

This application claims priority to Chinese application No. 201810145525.2, entitled "Methods for Preparing Resistant Dextrin by Using Compound Enzymes", filed Feb. 12, 2018, the content of which is herein incorporated by reference in its entirety.

BACKGROUND OF THE INVENTION

Field of the Invention

The present invention relates to a method for preparing a resistant dextrin by using compound enzymes (combination of multiple enzymes), and belongs to the technical field of enzyme engineering.

Description of the Art

Resistant dextrins are short chain glucose polymers obtained by high-temperature acidolysis of starch, which contains α-1,2 and α-1,3 glycosidic bonds in addition to the existing α-1,4 and α-1,6 glycosidic bonds in starch, and some reducing terminuses may contain β-1,6 glycosidic bonds. The α-1,3, α-1,2 and α-1,6 glycosidic bonds cannot be decomposed by various digestive enzymes in the human body, and cannot be digested and absorbed by the small intestine after entering the human digestive tract. Therefore, the dextrin with α-1,3, α-1,2 and α-1,6 glycosidic bonds can enter the large intestine and be used by various probiotics in the large intestine as nutrients to achieve various physiological functions of dietary fibers. The resistant dextrin can also create a feeling of satiety, thus being able to be used as a good auxiliary base material to be added to food for people with obesity. Clinical experiments also prove that the resistant dextrin has a certain effect on people with obesity. In addition, researchers also find that the resistant dextrin can also reduce cholesterol in mice with high cholesterol. It is likely that the resistant dextrin reduces the absorption efficiency of bile salts and cholesterol. It is possible to use the resistant dextrin to prevent hypercholesterolemia in the near future.

The resistant dextrin has no sweet taste and can be easily dissolved in water and beverages. It can maintain the original taste of a food when used as a food additive. It has unique potential to be used as a food additive as it can not only improve the taste and flavor of beverages but also have good solubility. The resistant dextrin can also remain stable under conditions such as high temperature, humid environment and a broad range of pH conditions. The resistant dextrin also has other benefits, such as low blood sugar response and slow heat release, which are very beneficial to those who want to control their weight. The resistant dextrin is also very beneficial to the peristalsis of the intestinal tract and can facilitate defecation. The resistant dextrin also has strong acid resistance, heat resistance, good solubility, and low viscosity. In 2012, the Department of Health of China declared the resistant dextrin as a common food in the announcement No. 16. The resistant dextrin and related products have now attracted the attention of many enterprises in the society. Because of the wide range of raw materials for producing the resistant dextrin, low production cost and safe and reliable production process, the application of the resistant dextrin in food industry will become more and more widespread.

Branching enzyme (BE for short, EC 2.4.1.18) belongs to the glycoside hydrolase family (GH13). The enzyme can be widely used to modify starch and catalyze the formation of α-1,6 glycosidic bonds. The main functions of the enzyme are, on the one hand, to catalyze the degradation of donor linear α-1,4 glucan chains (amylose and amylopectin), and on the other hand, to connect degraded donor fragments to receptors through the α-1,6 glycosidic bonds to form more branched chains, thus changing the degree of starch branching. The enzyme has important physical and chemical properties and physiological functions.

Cyclodextrin glycosyltransferase (EC 2.4.1.19, hereinafter referred to as CGTase) is a multi-functional enzyme which can catalyze four reactions: disproportionation reaction (intermolecular transglycosylation), hydrolysis reaction, cyclization reaction (intramolecular transglycosylation) and coupling reaction (reverse reaction of cyclization). Disproportionation reaction is the main reaction of the CGTase. This reaction cuts off one straight-chain maltooligosaccharide and transfers the cut-off intermediate product to another receptor, making a longer receptor chain. Various dextrins, carbohydrate chains and starch molecules can be used as glycosyl donors of the CGTase to produce glycosides under the hydrolysis reaction and the coupling reaction, and the glycoside is connected to a receptor chain through the disproportionation reaction. In this way, the structure of receptor molecules can be changed to improve their performance.

The research on the resistant dextrin in China started relatively late and, production capacity is low. Only a few companies can produce more than 10,000 tons of resistant dextrin per year. A large number of studies have shown that the method for preparing the resistant dextrin from starch by high-temperature acidolysis can only produce a pyrodextrin with about 40% resistant dextrin. The method not only has complicated separation and purification processes, but also leads to low utilization rate of raw materials (<40%), thus it is difficult to meet the needs of mass consumption due to the high cost. Therefore, there is an urgent need for developing new methods for preparing the resistant dextrin with an improved utilization rate of raw materials and an increased content of the resistant component.

DETAILED DESCRIPTION

Definitions:

Unless otherwise defined, all technical and scientific terms used herein have the same meaning as commonly understood by one of the ordinary skill in the art to which this invention belongs.

The term "dextrin", as used herein, refers to low-molecular-weight carbohydrates produced by the hydrolysis of starch. Dextrins can be produced from starch by enzyme digestion or by applying heat under acid conditions.

The term "resistant dextrin", as used herein, refers to dextrins that are resistant to digestive enzymes in the small intestine. The resistant dextrin contains α-1,2 and α-1,3 glycosidic bonds in addition to the existing α-1,4 and α-1,6 glycosidic bonds in starch, and some reducing terminuses of the resistant dextrin may contain β-1,6 glycosidic bonds. The α-1,3, α-1,2 and α-1,6 glycosidic bonds cannot be decomposed by various digestive enzymes in the human body, contributing to its enzyme resistance. It can be obtained by high-temperature degradation of starch under acid conditions or by digestion of selective enzymes.

The term "pyrodextrin", as used herein, refers to a product obtained by high-temperature degradation of starch under acid conditions. The pyrodextrin contains a mixture of starch degradation products with about 40% resistant dextrin.

The term "resistant dextrin product", as used herein, refers to a starch degradation product, part of which contains resistant dextrins. The "resistant content" of a resistant dextrin product refers to the portion of the resistant dextrins within the product, which contains α-1,2 and α-1,3 glycosidic bonds in addition to the existing α-1,4 and α-1,6 glycosidic bonds.

In order to solve the above-mentioned problems, the invention provides a method for preparing a resistant dextrin product by using compound enzymes, which reduces the production cost of and improves the percentage of the resistant component in the product.

In one embodiment of the present invention, starch is used as a substrate. The substrate is first subjected to high-temperature acidolysis to obtain pyrodextrin. A starch branching enzyme (SBE) and a CGTase are then added to the pyrodextrin simultaneously or successively. The resistant dextrin product is obtained after an appropriate period of enzymolysis reaction. The pyrodextrin refers to a product which is obtained by high-temperature acidolysis of starch and contains about 40% of the resistant dextrin.

In one embodiment, the starch branching enzyme is obtained from Thermuobifida fusca (TfSBE).

In one embodiment, the pyrodextrin is dissolved in a buffer (pH 6-7) at a concentration of 2% (g/100 ml).

In one embodiment of the present invention, the substrate is first subjected to high-temperature acidolysis to obtain the pyrodextrin, and then starch branching enzyme (1000-1500 U/g pyrodextrin) is added to the pyrodextrin to react for 8-12 hours at 35-50° C.

In another embodiment of the present invention, the substrate is first subjected to high-temperature acidolysis to obtain the pyrodextrin. Starch branching enzyme (1000-1500 U/g pyrodextrin) is added to the pyrodextrin to react for 8-12 hours at 35-50° C., and then the CGTase is added, wherein the addition amount of the CGTase is 5-10 U/g pyrodextrin, the reaction time is 10-12 hours, the reaction temperature is 30-40° C., and the pH value is 6.0-7.0.

In one embodiment of the present invention, the substrate is first subjected to high-temperature acidolysis to obtain the pyrodextrin, and then the starch branching enzyme (1000-1500 U/g pyrodextrin) and the CGTase (5-10 U/g pyrodextrin) are added to the pyrodextrin simultaneously to react for 8-12 hours at 30-40° C., pH 6.0-7.0.

In one embodiment of the present invention, the substrate is first subjected to high-temperature acidolysis to obtain the pyrodextrin, CGTase (5-10 U/g pyrodextrin) is added to the pyrodextrin to react for 4-6 hours at 40-50° C., pH 5.5-6, and starch branching enzyme (1000-1500 U/g pyrodextrin) is then added to react for 10-12 hours at 30-40° C., pH 6.0-7.0.

In one embodiment of the present invention, the high-temperature acidolysis is to add 1 mol/L HCl solution to the starch at a 5% ratio (w/w) and react at 160-200° C., and the pyrodextrin is obtained after cooling and sieving.

In one embodiment of the invention, the substrate is first subjected to high-temperature acidolysis to obtain the pyrodextrin; a starch branching enzyme (1000-1500 U/g pyrodextrin) derived from Thermuobifida fusca is added to the pyrodextrin and react at 30-40° C., pH 6.0-7.0, for 10-12 hours; and then the CGTase (5-10 U/g pyrodextrin) is added and react at 30-40° C., pH 6.0-7.0, for 10-12 hours.

In one embodiment of the invention, the starch branching enzyme is a starch branching enzyme derived from Thermuobifida fusca (TfSBE) with the amino acid sequence of SEQ ID NO.2. Preferably, the starch branching enzyme is produced by a recombinant bacterium such as E. coli that expresses a TfSBE gene shown in SEQ ID NO.1; preferably, the recombinant bacterium is E. coli BL21, E. coli JM109, E. coli DH5α or E. coli TOP10, and the expression vector is pT7-7. Preferably, the recombinant bacterium is constructed by inserting the TfSBE gene into the expression vector pT7-7 to obtain recombinant vector pT7-7-TfSBE, transforming the expression vector pT7-7-TfSBE into E. coli BL21 (DE3), and screening for positive transformants with pT7-7-TfSBE to obtain pT7-7-TfSBE/E. coli BL21 (DE3).

This is the first report to use pyrodextrin as a substrate and compound enzymes to make a resistant dextrin product. The content of the resistant component in the resistant dextrin product can reach up to 65.3%, a 21.3% increase from the pyrodextrin prepared from acidolysis.

EXAMPLES

Figure 1:
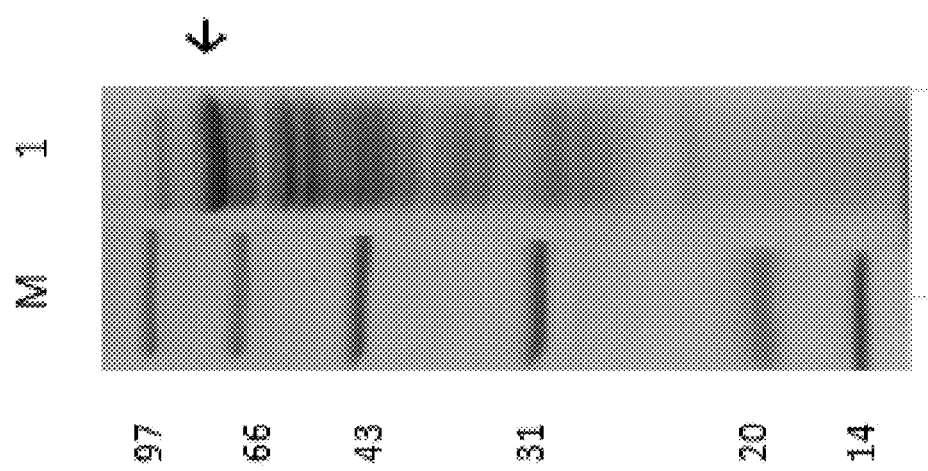
FIG. 1 shows an SDS-PAGE electrophoresis graph of a wall-broken supernatant (shake flask) of OD=5 recombinant bacteria fermentation; M: molecular weight markers; 1, E. coli BL21(DE3)/pT7-7-TfSBE cell wall-broken supernatant.

The technical details of some embodiments of the present invention are further described and illustrated below with reference to the accompanying drawings in the following examples. The examples are described only for illustration purpose, not to limit the scope of the present invention which is defined by the claims hereafter.

1. Method for Determining the Activity of a Starch Branching Enzyme:

(1) Preparation of 50 mM phosphoric acid buffer solution ($Na_2HPO_4 \cdot 12H_2O$ and $NaH_2PO_4 \cdot 2H_2O$) with a pH value of 6.5;

preparation of a Lugol's iodine solution: 0.26 g of iodine and 2.6 g of potassium iodide are dissolved in a 10 ml volumetric flask (prepared 3 days in advance to ensure complete iodine dissolution) and stored in the dark at room temperature;

preparation of a termination reaction solution: 0.1 mL of Lugol's iodine solution and 50 μL of 2 mol/L hydrochloric acid solution are mixed to the volume of 26 ml for immediate use;

preparation of a substrate solution: 0.01 g of amylose (or 0.1 g of amylopectin) and 0.2 ml of 96% ethanol are mixed, 0.5 mL of 2 mol/L NaOH solution is added after 3-4 minutes, 10 mL of water is added, the mixture is stirred for 10 minutes to dissolve starch, then 0.5 mL of 2 mol/L HCl solution is added, a buffer solution with a pH value of 6.5 is added to the volume of 10 mL, and the pH value is adjusted to 6.5.

(2) Determination of the activity of the SBE: 50 μL of enzyme solution and 50 μL of substrate are incubated in a water bath at 40° C. for 30 minutes. 2 mL of termination reaction solution is added, and absorbance is measured at 660 nm (amylose) or 530 nm (amylopectin) after standing at room temperature for 20 minutes. Definition of the activity of the SBE: the 660 nm or 530 nm absorbance decreasing by 1% per minute at room temperature is defined as one activity unit.

2. Method for determining the content of a resistant dextrin: the determination of the resistant dextrin refers to GB/T22224-2008 "Determination of dietary fiber in food-Enzyme gravimetric method".

Yield (%) of resistant dextrin=weight of dried substance/weight of pre-reaction pyrodextrin*100%.

Example 1: Construction of a Recombinant SBE-Expressing E. coli

A pair of primers P1 and P2 were designed according to the sequence of an SBE encoding gene, Tfu_0582 (GenBank accession number NC_007333.1:663757-666006). The underlines indicate cleavage sites for Nde I and Hind III.

```
                                                (SEQ ID No: 3)
P1: 5'-CCATATGACCGCCCGGCCTGCAGT-3'

(SEQ ID No: 4)
P2: 5'-CAAGCTTTCACGTCCCGTCGAACACCAGC-3'
```

The SBE gene Tfu_0582 was amplified by PCR using total DNA of *Thermuobifida fusca* (*T. fusca*) WSH03-11 as the template and P1 and P2 as primers (Chen, S. et al. *Journal Biol. Chem.*, 2008, 283 (38): 25854-62). The gene was ligated into a pMD18-T simple vector (Takara Bio, Beijing, China), the ligation product was transformed into *E. coli* JM109. The transformation product was coated on an LB plate containing 100 mg/L ampicillin. After culturing at 37° C. overnight, a colony was selected and cultured an LB liquid medium. A plasmid was extracted from the cultured colony after 8-10 hours and named Tfu_0582/pMD18-T simple, and sequence determination was conducted on the plasmid. Results showed that an insert fragment was a 2250 bp DNA fragment encoding the enzyme shown in SEQ ID NO.2.

Construction of an *E. coli* expression vector pT7-7 with the SBE gene was as following. The pT7-7 plasmid and Tfu_0582/pMD18-T simple were subjected to Nde I and Hind III double-enzyme digestion, respectively. The enzyme-digested products were purified by a gel extraction and were connected by a T4 ligase. The ligation product was transformed into *E. coli* JM109 competent cells. After 8 hours of culture at 37° C., transformants were picked from a LB shaking culture containing 100 mg/L kanamycin, and a plasmid was extracted which was verified to be an SBE gene-containing expression plasmid, named Tfu_0582/pT7-7, by enzyme digestion.

The plasmid Tfu_0582/pT7-7 was transformed into *E. coli* BL21(DE3) host bacteria and cultured in an LB plate containing kanamycin (100 mg/L) at 37° C. for 8 hours. A single kanamycin-resistant colony was picked and cultured in the liquid LB overnight at 37° C. The selected colony, which was an SBE-expressing *E. coli*, was preserved in a glycerol tube.

Example 2: Production of the SBE Using the Recombinant SBE-Expressing E. coli

The SBE-expressing *E. Coli* obtained in Example 1 was transferred into an LB medium for liquid culture at 37° C. overnight, and then inoculated into a TB fermentation liquid medium (glycerol 5 g/L, peptone 12 g/L, yeast extract 24 g/L, $K_2HPO_4$ 12.54 g/L, $KH_2PO_4$ 2.31 g/L) and cultured at 37° C. It was induced by isopropylthio-β-D-galactoside (IPTG) with a final concentration of 0.12-0.2 mm/L. After $OD_{600}$ reached 0.6, it was then cultured at 25° C. for 48 hours. The cells were collected by centrifugation and were suspended in a 0.05 mol/L sodium phosphate buffer solution (pH 6.5). The suspended cells were subjected to ultra-sonication. The activity of the SBE in the supernatant was measured, and the activity of the recombinant SBE reached 2,500 U/mL. FIG. 1 shows an SDS-PAGE electrophoresis graph of the recombinant SBE protein.

Figure 2:
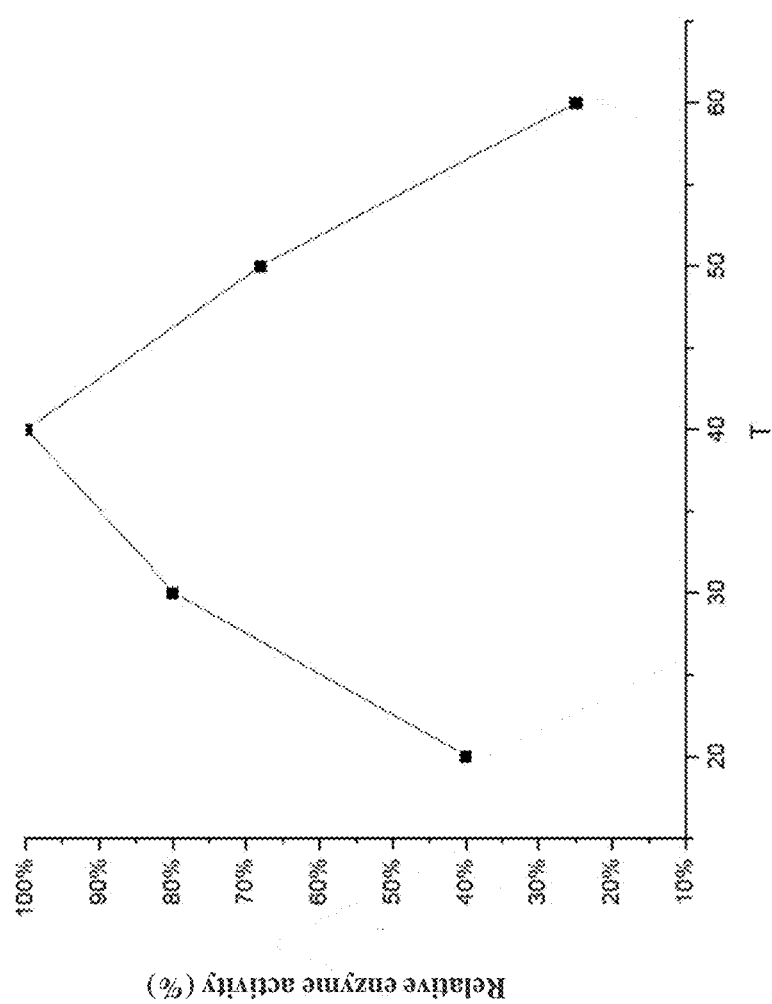
FIG. 2 shows the activity of a starch branching enzyme at different temperatures.
Figure 3:
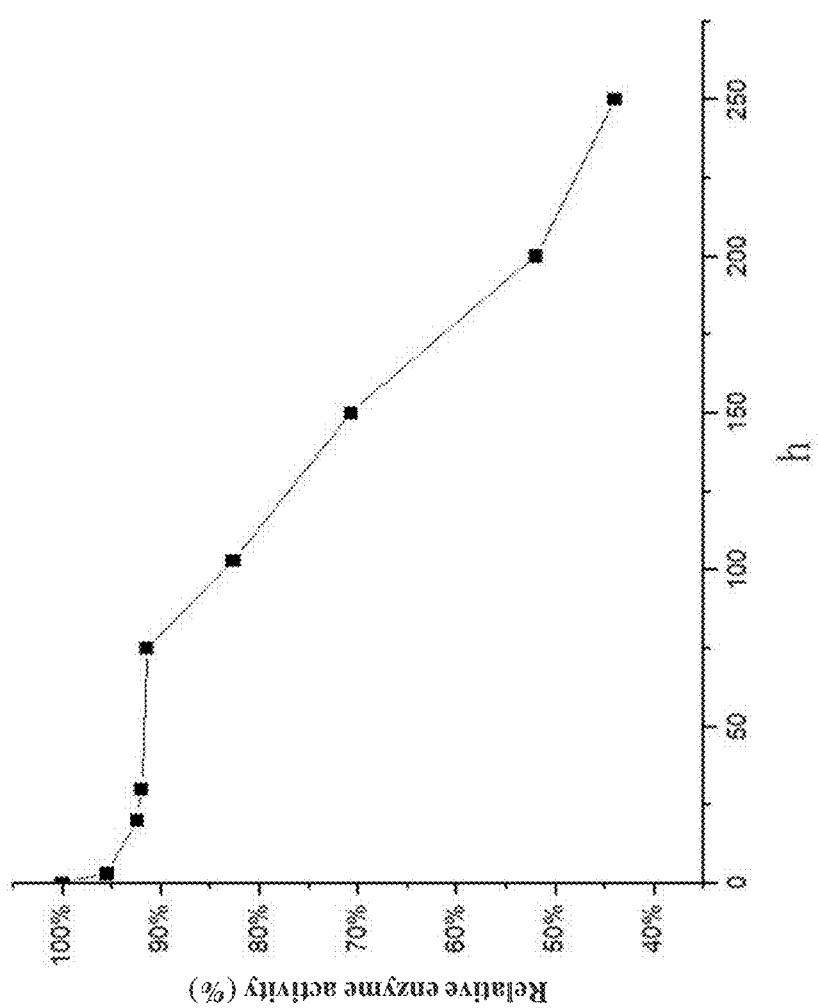
FIG. 3 shows the thermal stability of the starch branching enzyme at 40° C.
Figure 4:
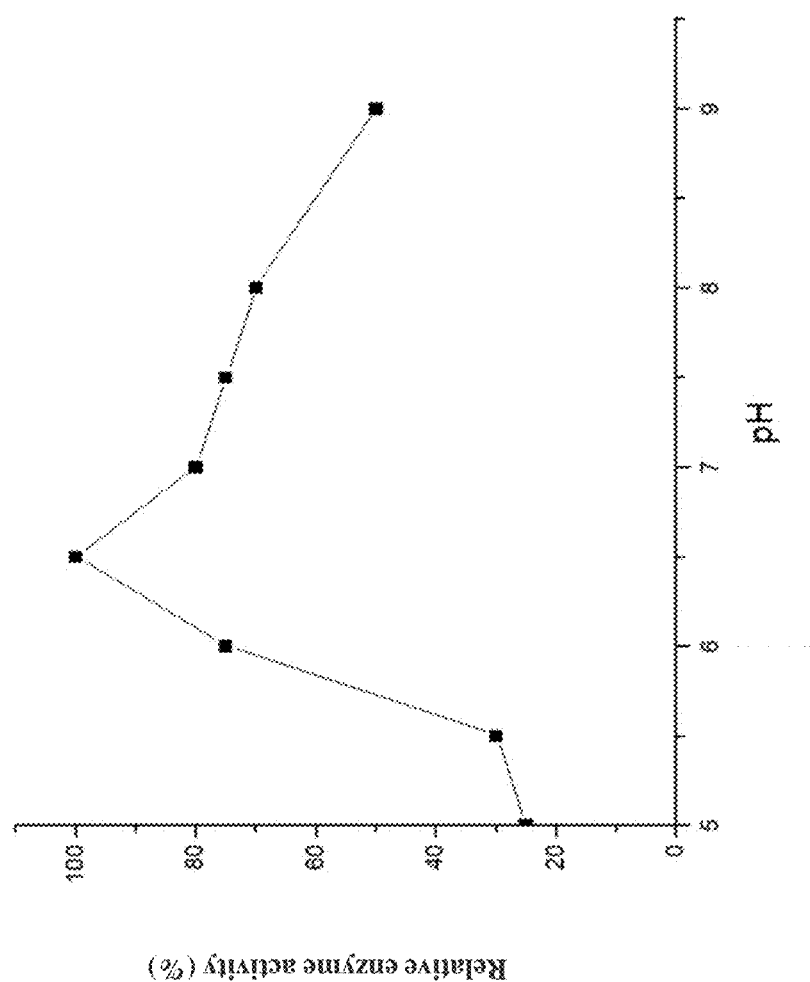
FIG. 4 shows the activity of the starch branching enzyme at different pH values.

Amylose was used as the substrate, and the enzyme activity was measured at different temperatures. Results showed that the optimum temperature of the starch branching enzyme was 40° C. (FIG. 2) and the half-life at 40° C. was 200 hr (FIG. 3). The activity of the starch branching enzyme was measured at different pHs under the optimum temperature condition, and the optimum pH value of the enzyme was shown to be 6.5 (FIG. 4).

Example 3: Application of Starch Branching Enzyme in Preparation of the Resistant Dextrin Starch was used as a substrate for preparation of resistant dextrin. 5% of 1 mol/L HCl solution was added to starch for high-temperature reaction at 160-200° C. to obtain a pyrodextrin solution, and the content of the resistant dextrin in the pyrodextrin solution reached 40%-45% after cooling and sieving. The pyrodextrin solution was prepared into 200-300 g/L solution. An enzyme conversion was performed by adding an SBE to the pyrodextrin solution. The enzyme conversion was conducted at different temperatures, and it was found that the optimum conversion temperature of a starch branching enzyme obtained from *T. fusca* WSH03-11 was 35-45° C. By conducting the enzyme conversion under different pH conditions, it was found that enzyme conversion efficiency was the highest at the pH 6-7. By performing the enzyme conversion under different enzyme concentrations and different reaction times, it was found that the optimum range of the enzyme concentration was 1000-1500 U/g pyrodextrin and the optimum range of the reaction time was 8-12 hours.

Figure 5:
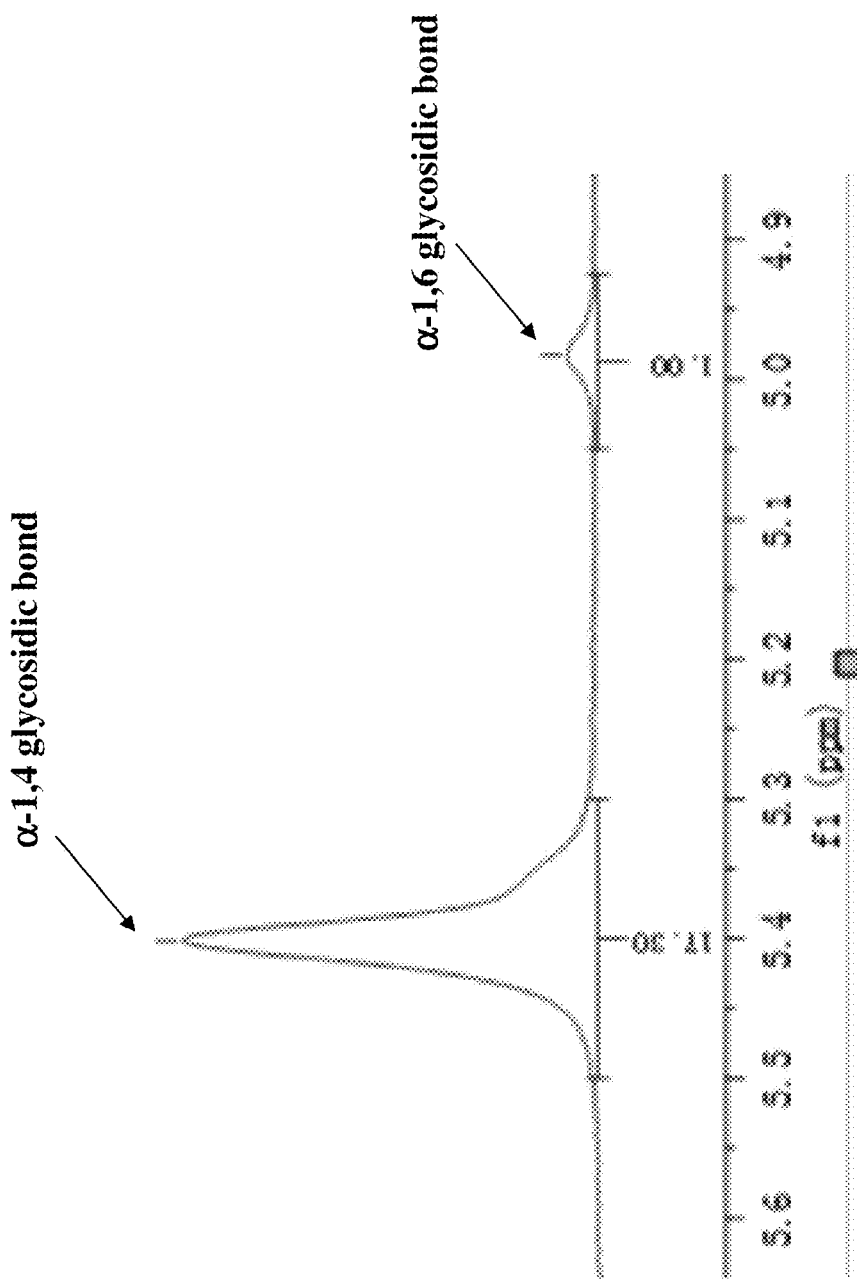
FIG. 5 shows the ratio of α-1,4 glycosidic bond to α-1,6 glycosidic bond in starch.
Figure 6:
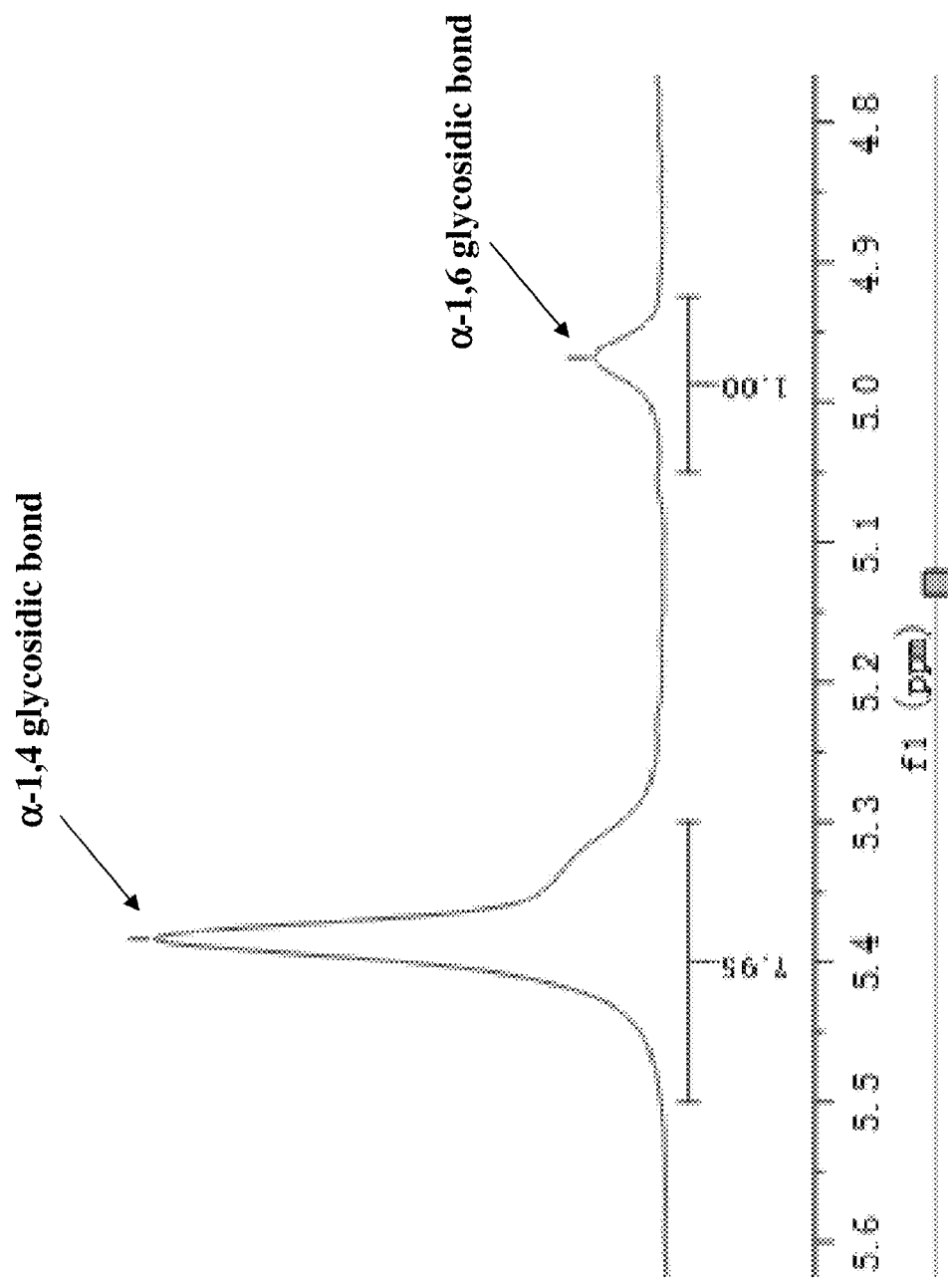
FIG. 6 shows the ratio of α-1,4 glycosidic bond to α-1,6 glycosidic bond in a resistant dextrin.

According to the above conditions, 5% of 1 mol/L HCl solution was added to starch for high-temperature reaction at 160-200° C. to obtain a pyrodextrin solution with 40%-45% resistant dextrin. The starch branching enzyme prepared in Example 2 (1000-1500 U/g pyrodextrin) was added to the pyrodextrin solution and incubate at 35-45° C., pH 6-7 for 8-12 hours to obtain a resistant dextrin crude product with increased content of resistant dextrin. The content of the resistant dextrin in the pyrodextrin was increased in the enzyme treated product by 10% compared with that of the pyrodextrin before the enzyme treatment. The obtained resistant dextrin crude product and the starch were detected by a nuclear magnetic resonance method, as shown in FIG. 5 and FIG. 6 (two local maps under the same signal intensity). The ratio of α-1.4 glycosidic bonds to α-1.6 glycosidic bonds in the starch and the resistant dextrin crude product was changed. The ratio of α-1.4 glycosidic bonds: α-1.6 glycosidic bonds before and after the SBE treatment is 17.5 and 7.95, respectively, showing that the amount of the α-1.4 glycosidic bonds decreased while the amount of the α-1.6 glycosidic bonds increased due to the SBE treatment.

Example 4: Application of a Starch Branching Enzyme of *Thermus thermophiles* in Preparation of the Resistant Dextrin Starch was used as a substrate for preparation of the resistant dextrin. 5% of 1 mol/L HCl solution was added to starch for high-temperature reaction at 160-200° C. to obtain a pyrodextrin solution with 40%-45% resistant dextrin. The pyrodextrin solution was prepared into 200-300 g/L solution. A starch branching enzyme of *Thermus thermophiles* (2500-3000 U/g pyrodextrin) was added for enzyme conversion at 60-65° C., pH 6-7, for 10-12 hours. The content of the resistant dextrin in the pyrodextrin solution was increased in the enzyme treated product by 5% compared with that before the enzyme treatment.

Example 5: Application of Starch Branching Enzyme AaBE of *Aquifex Aeolicus* in Resistant Dextrin Starch was used as a substrate for preparation of the resistant dextrin. 5% of 1 mol/L HCl solution was added to starch for high-temperature reaction at 160-200° C. to obtain a pyrodextrin solution with 40%-45% resistant dextrin. The pyrodextrin solution was prepared into 200-300 g/L solution. The AaBE branching enzyme (3000 U/g pyrodextrin) was added for enzyme conversion at 70-80° C., pH 7.0-7.5, for 10-12 hours. The content of the resistant dextrin in the pyrodextrin solution was increased in the enzyme treated product by 3% compared with that before the enzyme treatment.

Comparative Example 1

The experimental condition was similar to that of Example 3 except that the enzyme reaction temperature was 30° C. The content of the resistant dextrin in the pyrodextrin solution was increased in the enzyme treated product by 6-7% compared with that before the enzyme treatment.

Comparative Example 2

The experimental condition was similar to that of Example 3 except that the pH of the enzyme conversion reaction was 5 or 8. The content of the resistant dextrin in the pyrodextrin solution was increased in the enzyme treated product by 2.5-3% compared with that before the enzyme treatment.

Comparative Example 3

The experimental condition was similar to that of Example 3 except that the enzyme reaction time was less than 8 hours. The content of the resistant dextrin in the pyrodextrin solution was increased in the enzyme treated product by 2-8% compared with that before the enzyme treatment. However, when the enzyme reaction time was more than 12 hours, the increase of the resistant dextrin was basically unchanged.

Comparative Example 4

The experimental condition was similar to that of Example 2 except that IPTG induction was not carried out, and results showed that the activity of the branching enzyme was about 500 U/mL.

Example 6: Effect of Successively Adding TfSBE and CGTase on Increasing the Content of Resistant Dextrin in Pyrodextrin Starch was used as a substrate for preparation of the resistant dextrin. 5% of 1 mol/L HCl solution was added to starch for high-temperature reaction at 160-200° C. to obtain a pyrodextrin solution with 40%-45% resistant dextrin. 2 g/100 mL pyrodextrin was used as a substrate to prepare a resistant dextrin product using the optimum catalytic reaction conditions for the TfSBE, that is, a pH value of 6.0-7.0, a temperature of 30-40° C., an enzyme amount of 1000-1500 U/g pyrodextrin and a reaction time of 10-12 hours. After that, 5-10 U/g pyrodextrin of CGTase was added, and the reaction was continued for another 10-12 hours at the pH 6.0-7.0 and 30-40° C. (the CGTase still has about 70% of enzyme activity under this condition). After the reaction was finished, the enzyme was inactivated by boiling water, and the yield of the resistant component at different time points was detected by using the resistant dextrin content detection method as described above.

Figure 7:
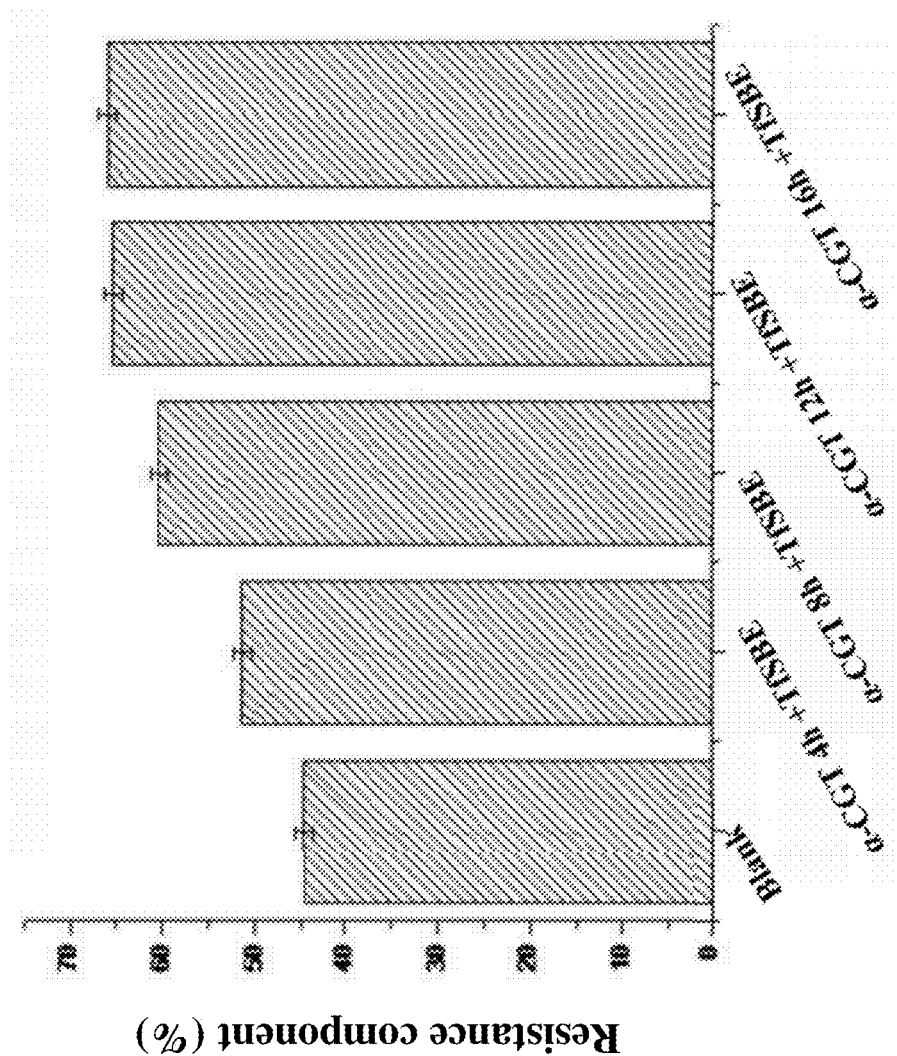
FIG. 7 shows that a TfSBE and a CGTase are added successively to increase the resistant component in the pyrodextrin.

As shown in FIG. 7, it was found that when the CGTase was added for 12-16 hours, i.e. the total catalytic time was 22-28 hours, the content of the resistant component reached the maximum value of 65.3%, 21.3% higher than that of the pyrodextrin product before the enzyme treatment (the blank group).

Example 7: The Effect of Adding CGTase and TfSBE Simultaneously on the Content of Resistant Dextrin in Pyrodextrin The optimum temperature and pH for the catalytic reaction of the CGTase is 40-50° C. and 5.5, respectively. Since the activity of the TfSBE is only about 30% of the optimum activity under pH 5.5, and the CGTase still has about 70% activity under the optimum temperature and pH conditions of the TfSBE, it is possible to add the two enzymes simultaneously under the optimum enzymatic conversion conditions of the TfSBE.

Figure 8:
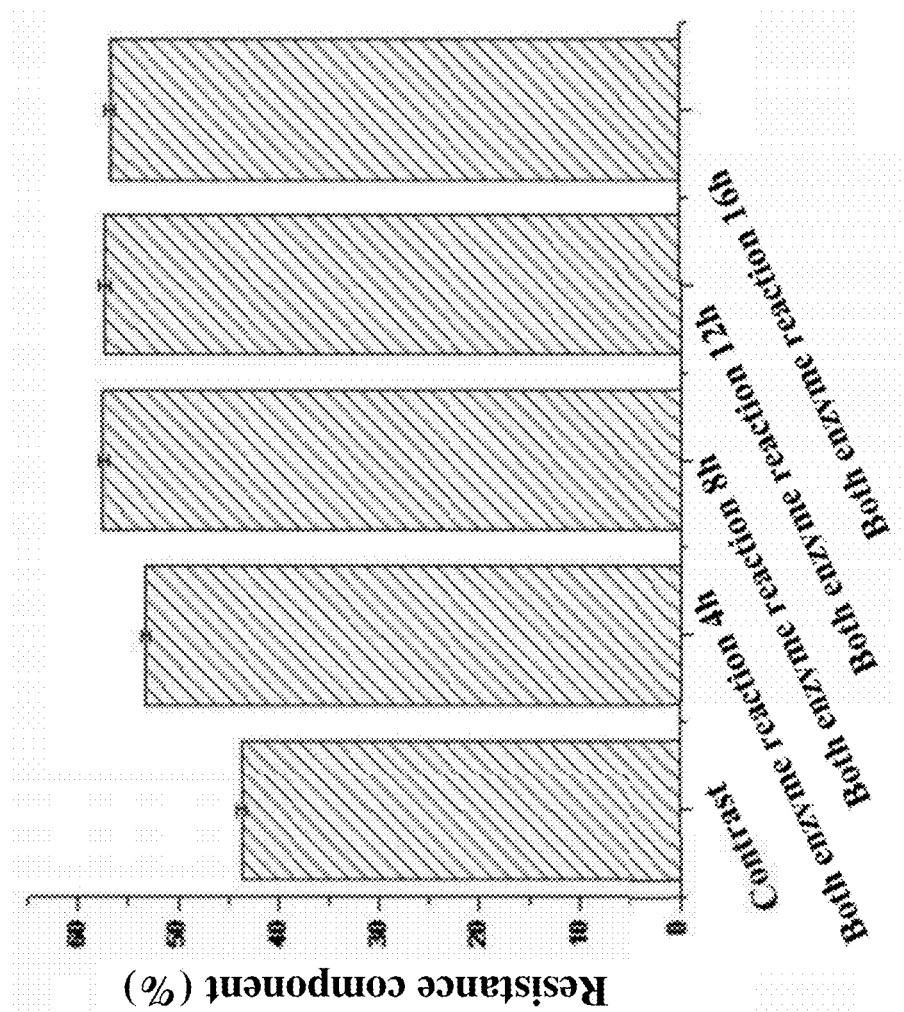
FIG. 8 shows that the CGTase and the TfSBE are added simultaneously to increase the resistant component in the pyrodextrin.

Starch was used as a substrate for preparation of the resistant dextrin. 5% of 1 mol/L HCl solution was added to starch for high-temperature reaction at 160-200° C. A pyrodextrin solution with 40%-45% resistant dextrin was obtained after cooling and sieving. 2% (g/100 mL) pyrodextrin was used as a substrate for enzyme treatment. The recombinant starch branching enzyme TfSBE prepared in Example 2 (1000-1500 U/g pyrodextrin) was added with the CGTase (5-10 U/g pyrodextrin) at 30-40° C., pH 6-7. The reaction time was 4, 8, 12 and 16 hours. After the reaction was finished, the enzymes were inactivated in a boiling water bath for 10 minutes, and the content of the resistance component in the final product was detected by the resistance component detection method as described above. As shown in FIG. 8, it can be found that when the reaction was proceeded for 8-12 hours, the content of the resistance component reached the maximum value of 57.49%, 13.8% higher than that of the pyrodextrin before enzyme treatment (blank group).

Figure 9:
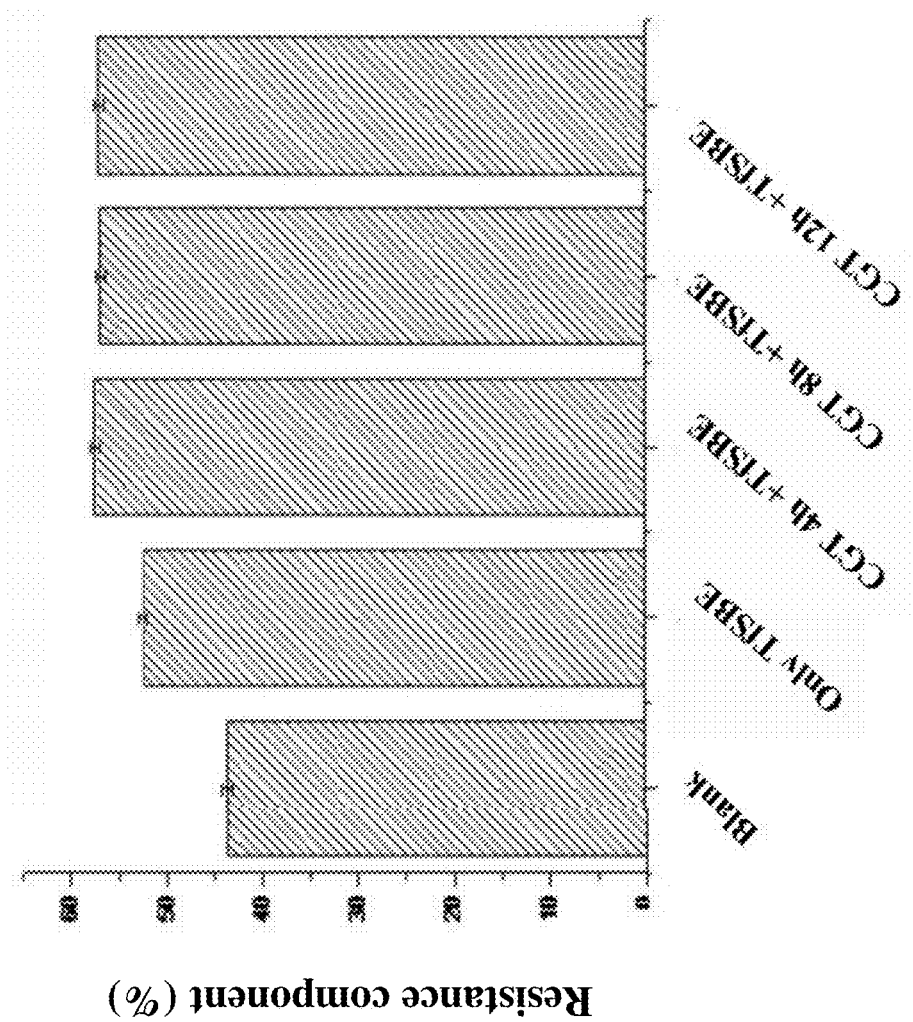
FIG. 9 shows that the CGTase and the TfSBE are added successively to increase the resistant component in the pyrodextrin.

Example 8: Effect of Successively Adding CGTase and TfSBE on Increasing Content of Resistant Component in Pyrodextrin Starch was used as a substrate for preparation of pyrodextrin. 5% of 1 mol/L HCl solution was added to starch for high-temperature reaction at 160-200° C., and the pyrodextrin was obtained after cooling and sieving. 2% (g/100 mL) pyrodextrin was used as a substrate for enzyme treatment. The enzyme catalytic reaction was carried out under the optimum condition for the reaction of the CGTase (40-50° C., pH 5.5), the enzyme addition amount was 5-10 U/g, the reaction time was 4, 8 or 12 hours. The pH value was then adjusted to 6-7, the optimum recombinant TfSBE was added at 30-40° C., the enzymes were inactivated by a boiling water bath after 10-12 hours of reaction. The content of the resistant dextrin was detected by the resistance dextrin detection method as described above. As shown in FIG. 9, it can be found that when the CGTase reacted for 4 hours and the recombinant TfSBE was added to react for 10-12 hours, the content of the resistant dextrin reached the maximum of 57.5%, 13.7% higher than that of the pyrodextrin before enzyme treatment.

Figure 10:
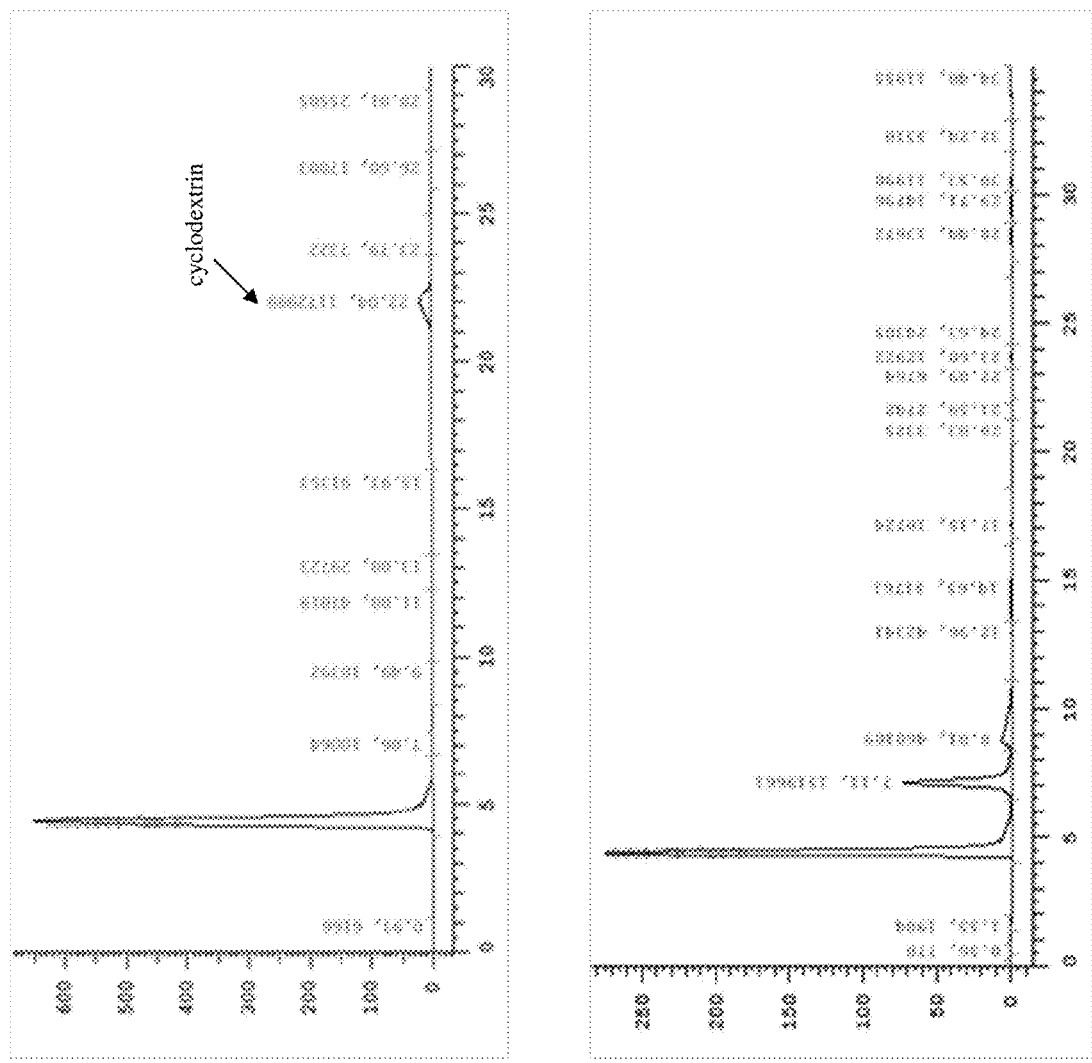
FIG. 10 shows HPLC analysis of components in the pyrodextrin after the CGTase and the TfSBE treatment; (a) a cyclodextrin standard sample; (b) a sample after the reaction of the CGTase and the TfSBE.

In order to confirm that the product was not cyclodextrin, HPLC analysis was carried out on the product. As shown in FIG. 10, it was found that there was no cyclodextrin corresponding peak in the HPLC map of the enzyme treated product, indicating that the product had no detectable cyclodextrin. Addition of the CGTase significantly increased the content of the resistant dextrin. By combining the above experimental methods, it shows that the combined treatment of pyrodextrin with the SBE and the CGTase enzymes can increase the content of the resistant dextrin up to 65.3%, 21.3% higher than that of the original pyrodextrin.

While the present invention has been described in some detail for purposes of clarity and understanding, one skilled in the art will appreciate that various changes in form and detail can be made without departing from the true scope of the invention. All figures, tables, appendices, patents, patent applications and publications, referred to above, are hereby incorporated by reference.

---

What is claimed is:

1. A method for preparing a resistant dextrin product, comprising adding a starch branching enzyme and a cyclodextrin glycosyltransferase (CGTase) to a pyrodextrin simultaneously or successively, wherein the starch branching enzyme is obtained from *Thermobifida fusca*, having the amino acid sequence of SEQ ID NO: 2, and the CGTase has the amino acid sequence of SEQ ID NO:5, wherein 1000-1500 U/g pyrodextrin of the starch branching enzyme and 5-10 U/g pyrodextrin of the CGTase is added to the pyrodextrin simultaneously or successively.

2. The method of claim 1, comprising performing high-temperature acidolysis of starch to obtain the pyrodextrin.

3. The method of claim 2, wherein 1000-1500 U/g pyrodextrin of the starch branching enzyme is added to the pyrodextrin and react at 35-50° C. for 8-12 hours.

4. The method of claim 3, further comprising adding 5-10 U/g pyrodextrin of the CGTase to the pyrodextrin and reacting at 30-40° C., pH 6.0-7.0 for 10-12 hours.

5. The method of claim 1, wherein 1000-1500 U/g pyrodextrin of the starch branching enzyme and 5-10 U/g pyrodextrin of the CGTase are simultaneously added to the pyrodextrin and react at 30-40° C., pH 6.0-7.0 for 8-12 hours.

6. The method of claim 2, comprising adding 5-10 U/g pyrodextrin of the CGTase to the pyrodextrin and reacting at 40-50° C., pH 5.5-6 for 4-6 hours, and then adding 1000-1500 U/g pyrodextrin of the starch branching enzyme and reacting at 30-40° C., pH 6.0-7.0 for 10-12 hours.

7. The method of claim 2, wherein the high-temperature acidolysis is adding 5% of 1 mol/L HCl solution to the starch and react at 160-200° C., and the pyrodextrin is obtained after cooling and sieving of the acidolysis product.

8. The method of claim 2, comprising adding a starch branching enzyme obtained from *Thermobifida fusca* to the pyrodextrin, wherein the amount of the starch branching enzyme is 1000-1500 U/g pyrodextrin, the reaction temperature is 30-40° C., the pH range is 6.0-7.0, and the reaction time is 10-12 hours; and then adding the CGTase to the reaction, wherein the amount of the CGTase is 5-10 U/g pyrodextrin, the reaction time is 10-12 hours, the reaction temperature is 30-40° C., and the pH range is 6.0-7.0.

9. The method of claim 1, wherein the starch branching enzyme is produced by a recombinant *E. coli* containing a starch branching enzyme gene of SEQ ID NO:1.

10. The method of claim 1, wherein the concentration of the pyrodextrin is 2 g/100 ml in a pH 6.0-7.0 buffer.

11. The method of claim 5, comprising performing high-temperature acidolysis of starch to obtain the pyrodextrin.

12. The method of claim 5, wherein the high-temperature acidolysis is adding 5% of 1 mol/L HCl solution to the starch and react at 160-200° C., and the pyrodextrin is obtained after cooling and sieving of the acidolysis product.

13. The method of claim 5, wherein the starch branching enzyme is produced by a recombinant *E. coli* containing a starch branching enzyme gene of SEQ ID NO:1.

14. The method of claim 5, wherein the concentration of the pyrodextrin is 2 g/100 ml in a pH 6.0-7.0 buffer.

* * * * *